US009248297B2

(12) United States Patent
Høyer et al.

(10) Patent No.: US 9,248,297 B2
(45) Date of Patent: Feb. 2, 2016

(54) SYSTEM FOR ELECTRICAL STIMULATION OF NERVES (75) Inventors: Michael Høyer, Aalborg (DK); Clemens Florian Eder, London (GB); Morten Hansen, Storvorde (DK)

(73) Assignee: NEURODAN A/S, Aalborg (DK)

( * ) Notice: Subject to any disclaimer, the term of this patent is extended or adjusted under 35 U.S.C. 154(b) by 0 days.

(21) Appl. No.: 13/516,183

(22) PCT Filed: Dec. 15, 2010

(86) PCT No.: PCT/DK2010/000175
§ 371 (c)(1),
(2), (4) Date: Aug. 22, 2012

(87) PCT Pub. No.: WO2011/072683
PCT Pub. Date: Jun. 23, 2011

(65) Prior Publication Data
US 2013/0013026 A1    Jan. 10, 2013

(30) Foreign Application Priority Data
Dec. 15, 2009   (DK) .................................. 2009 01324

(51) Int. Cl.
*A61N 1/36* (2006.01)
*A61N 1/372* (2006.01)
*A61H 3/00* (2006.01)
A61B 5/04 (2006.01)

(52) U.S. Cl.
CPC .............. *A61N 1/37223* (2013.01); *A61H 3/00* (2013.01); *A61B 5/04001* (2013.01); *A61H 3/008* (2013.01); *A61N 1/36003* (2013.01); *A61N 1/36007* (2013.01); *A61N 1/36017* (2013.01)

(58) Field of Classification Search
CPC ........... A61N 1/36003; A61N 1/37223; A61B 5/04001; A61H 3/00; A61H 3/008
USPC ............................................................ 607/49
See application file for complete search history.

(56) References Cited

U.S. PATENT DOCUMENTS

| 5,289,827 | A  | * | 3/1994  | Orkin et al. ................... 600/588 |
| 5,991,661 | A  | * | 11/1999 | Park et al. ....................... 607/19 |
| 6,453,201 | B1 | * | 9/2002  | Daum et al. ..................... 607/62 |
| 7,403,821 | B2 | * | 7/2008  | Haugland et al. ............... 607/49 |
| 7,630,756 | B2 | * | 12/2009 | Linker .......................... 600/509 |
| 7,771,351 | B1 | * | 8/2010  | Talman et al. ................. 600/302 |
| 2002/0138009 | A1 | * | 9/2002 | Brockway et al. ............. 600/485 |
| 2004/0015208 | A1 |   | 1/2004 | Haugland et al. |
| 2009/0278798 | A1 | * | 11/2009 | Kim et al. ..................... 345/158 |
| 2010/0262044 | A1 | * | 10/2010 | Siegler et al. ................. 600/592 |

FOREIGN PATENT DOCUMENTS

WO    2007130168 A1    11/2007
WO    2009080784 A1    7/2009

OTHER PUBLICATIONS

PCT International Search Report for International Application No. PCT/DK2010/000175, mailed Feb. 9, 2011.

* cited by examiner

*Primary Examiner* — William Levicky
(74) *Attorney, Agent, or Firm* — Holland & Hart

(57) ABSTRACT

A system for treatment of gait disorders reflects, with electrical stimulation patterns fed to electrodes (1, 8) arranged at the patient, on the event of heel-strike and heel-off, the events being generated by a wireless heel switch (5). The pulse generator (4) also transfers the electrical energy needed to operate the heel switch (5) wirelessly. The event signal from the heel switch (5) is modulated in order to achieve a longer operating range.

14 Claims, 4 Drawing Sheets

$$Z_T = \frac{\omega^2 k^2 \cdot L_1 \cdot L_2}{R_2 + j\omega L_2 + Z_{TAG}}$$

SYSTEM FOR ELECTRICAL STIMULATION OF NERVES

TECHNICAL FIELD

The present invention is generally concerned with the art of electrical stimulation of nerves.

BACKGROUND OF THE INVENTION

Electrical stimulation of nerves or branches of nerves is known to be effective in the treatment of a variety of neurological disorders in living beings spanning from treatment of incontinence to gait disorders.

Treating gait disorders, especially correcting drop-foot, electrodes are placed in the proximity of the peroneal nerve or its branches. A pulse generator connected to the electrode generates a pattern of pulses to stimulate the nerve which will cause the foot dorsiflexor muscles to contract. Thus the foot will be lifted and it will be possible for the patient to swing the leg in a more natural manner. An example of a system for correction of drop-foot is known from U.S. Pat. No. 7,403,821 B2 to Neurodan A/S. The document covers the medical aspects and examples of various preferred embodiments are disclosed. For the triggering of the electrical stimulation of the nerve, according to the wanted reaction of the foot, the use of a foot switch is disclosed. Both the heel-off and heel-strike can be detected and used for input to the pulse generator in order to calculate and initiate the appropriate pulse pattern to be fed to the electrode. The foot switch can be connected to the pulse generator using electrical wires or the foot switch can include a wireless transmitter module for communicating the pulse generator.

Anyhow a disadvantage can be seen in that equipping the foot switch with a wireless transmitter module results in a quite voluminous device. This is especially the case taking into considerations that the foot switch when mounted on the foot has to be contained in or at least partly in the foot wear, partly protruding out of the foot wear. If the foot switch is kept in place under the foot by a sock or other means, e.g. bands, it presents even more of an obstacle. A voluminous device also tends to move its position in relation to the foot over time introducing another source of failure. Another disadvantage associated, is that a wireless module in the form of a wireless transmitter needs a source of energy in the form of a battery. Both the wireless transmitter and battery take up much space, and adds to the complexity of the housing and the costs of the mechanics. Additionally, the presence of a battery in itself introduces a limitation since it has to be replaced now and then or have to be recharged if the battery is rechargeable. The cost for a wireless transmitter module is also a factor that should be taken into account.

DESCRIPTION OF THE INVENTION

It is an object of the present invention to provide a system for stimulation of nerves with a trigger device, which is simpler, takes less space and takes away the need for replacement or recharge of batteries.

In a first aspect, the present invention provides A system for stimulation of nerves comprising:
At least one electrode,
A pulse generator for generating a pulse pattern to be forwarded to that at least one electrode and
A trigger device,
the pulse generator being configured to receive control signals wirelessly from the trigger device the trigger device is powered wirelessly from the pulse generator.

More detailed, the system for stimulation of nerves includes a programmable controller equipped with a pulse generator for generating a pulse pattern to be forwarded to at least one electrode adapted to be implanted in the corpus of the living being and/or at least one electrode adapted to be mounted on the surface of the skin for surface stimulation of nerves or muscles, the controller being equipped with a wireless transmitter for wirelessly communicating with a trigger device, the trigger device including means for sensing an event and means for communication with the controller and means for powering the trigger wirelessly from the transmitter.

In one embodiment, the pulse generator includes a transmitter that sends out broadcasts and the trigger device include means for inductive loading the transmitter, the inductive load being an oscillation circuit with a resonant frequency tuned into the frequency of the broadcasted signal. The broadcasted signal can be a continuously broadcasted signal or more expediently for the sake of saving energy a signal send out with regular intervals. It is preferred that the signal be send out so regularly that the trigger can be recognized within the required intervals.

More specific this is according to the invention provided by carrying out the trigger device to include an oscillation circuit tuned in at a specific frequency to match a corresponding transmitter, the transmitter being electrically connected to the pulse generator. In this way the trigger device can obtain electrical energy wirelessly from the transmitter by inductively loading the transmitter.

Further including means for sensing an event to the trigger device enables the trigger device to respond to the sensed event by changing the inductive loading of the transmitter.

In a simple embodiment the trigger device includes a switch that, when mechanically manipulated, activates or deactivates the inductive loading of the transmitter. In one embodiment the switch is a tactile switch adapted to be placed under the foot of a patient in order to reflect the events heel-strike and/or heel-off.

More specific, the oscillation circuit in the trigger device will form an open loop circuit when the switch is open and a closed loop when the switch is closed. The transmitter will be broadcasting a signal tuned in to the resonant frequency of the oscillation circuit. Thus when the switch is closed the oscillation circuit will appear as a load on transmitter. Measuring the load it will be possible to determine the state of the switch in the trigger if it is open or closed. The state of the switch will be corresponding to the event that manipulates the switch. Possible events for medical equipment could possibly be a triggering of a foot switch for a system treating gait disorders. In a system for the treatment of incontinence, the event could correspond to the event where the patient feel urge and toggles the switch in order to initiate a sequence of electrical pulses to be forwarded to the electrode.

Even though the trigger device has been explained with a trigger in the form of switch it is also in the scope of the invention to use other possible means for manipulating the oscillation circuit as a de-tuning capacitor, a variable capacitor, a variable resistor, by changing the resistance via a force sensitive resistor, a piezo electric element or in a more sophisticated way by using a logic control circuit for generating an analog or digital output, e.g. in form of a pulse pattern. The above mentioned triggering means can be used alone or in combination.

In another advantageous embodiment the oscillation circuit will be produced with a number of different tuning frequencies, so it is possible to distinguish at least a number of different trigger devices. This makes it possible for more users of trigger devices to have their stimulation system coexisting without risk for interference. Another suitable solution to the problem is to limit the operating range of the system, by lowering the transmitted power from the transmitter. Care must be taken to secure a reliable detection of the load of the trigger device. Having a number of individually triggers possible to identify, gives the opportunity of placing more trigger devices on the patient for the monitoring of different events. Placing more trigger devices under the patient's foot in specific positions will generate useful input to the signal generator for building an electric stimulation signal that fits better to the swing phase of that particular patient. In order to take advantage of the input, the transmitter must be capable of supporting more than one transmitter frequency.

In a further embodiment the trigger device and corresponding communication device is carried out in a way that improves the operating range of the system and enables a better unique identification of the trigger device. The trigger device will load the transmitter coil inverse proportional to the distance, so that loading will be weaker and weaker the longer the distance; hence the modulation of the primary carrier is so small to a point where it cannot be distinguished from other changes in the carrier (for example noise). To achieve a better separation of the load signal contribution from the carrier signal within a reasonable dynamic range, the trigger device is designed to create modulation products in a side band of the carrier, in order for the signal of interest to be easier separated from the carrier by means of filtering. To do this, the trigger device is further equipped with a logical unit that generates a pre-scaled subcarrier. This subcarrier is being modulated onto the carrier, whenever the trigger device is activated.

A system as described above, featuring pre-scaled subcarriers is in addition especially suited for a system where a stream of data is transferred. For a practical use of data transfer in the present invention, it would be appreciated if a unique identification could be included in a data stream. It can be foreseen that more detailed data that represent the event of triggering can be forming a data packet to be forwarded via the wireless link. It could be timestamps of triggering events with measurements of force for the individual trigger that are activated. Thus the data can be used to adapt the electrical nerve stimulation pattern to the specific gait of the patient in order to achieve a more natural gait and swing phase.

Using inductive coupling for a communication link, the magnetic field strength is decreasing rapidly with distance. In order to reach a longer operating range, a RFID system based on passive backscattering can provide a longer operating range. In this mode of operation, a wave of higher frequency (in the UHF range) is being broadcasted from the reader, and reflected by the transponder. The amount of reflection is determined by the load connected to the receiver antenna of the transponder, and the magnitude of the reflected wave can be detected by the receiver antenna of the reader. When transmitting in the UHF band, a region located a few meters away from the reader can be assumed as a far field region, in which the broadcasted wave is decreasing only indirectly proportional to the distance. Therefore, the field strength is decreasing by only 20 dB per decade distance increase, allowing a longer range of operation than in systems that are coupled inductively. Implementing the trigger device and reader as a passive backscatter system, the trigger device modulates the signal received from the transmitter by producing event-related changes in the reflexion coefficient. It has to be understood that a backscattering based system, in the same way as described under the inductive load system, can be designed to send data streams back to the reader. The data can possibly include timestamps of event and measurements of e.g. force or other properties of the event.

The event related changes can be obtained by sensors connected to the trigger device as the possible sensors described in the embodiment of the inductive loading. To sum up a sensor in the form of a switch could be used but it is also in the scope of the invention to use other possible means for manipulating the oscillation circuit as a de-tuning capacitor, a variable capacitor, a variable resistor, by changing the resistance via a force sensitive resistor, a piezo electric element or in a more sophisticated way by using a logic control circuit for generating an analog or digital output, e.g. in form of a pulse pattern. The above mentioned triggering means can be used stand alone or in combination.

The oscillation circuit and the switch can in a preferred embodiment be carried out on a mounting base made of a flexible material, preferably a foil or thin film. A plastic foil or film will be suited for the purpose because of its fine electrical isolation qualities. On one or more layers of foil the coil can be printed or applied using an electrical conducting material and the capacitor can be applied as a component or build up using more layers of film. The switch can be carried out on an area on the foil using one layer for the first connecting point and one layer for the second connecting point where the connection between the layers are maintained when the layers are pressed together and the connection between the layers are released when the press is released. In this way the trigger device is arranged on or in a compound made of one or more layers of foil. In another embodiment a contact dome is used for building a contact on the foil on which the coil and contact points has been carried out as on a printed circuit board. More layers of foil can be used to electrically isolate the device, e.g. as a sandwich build up. Adding an adhesive to at least one surface of the foil or part of the surface, the piece of film can in an easy way be placed in a position where the switch can be used to reflect on an event and serving as a triggering mechanism for an electrical stimulation system. In an appreciated embodiment, the trigger device is arranged on an adhesive plaster or sticker. The foil could be substituted by or added to a flexible fabric of the kind known from medical plasters. It could be embedded in the plaster or arranged under or on top of the plaster. Arranging the trigger device with a plaster has the further advantages that the flexible material supports the trigger device and adapts to the skin of the patient. Different types of plaster can be used depending on specific demands to create e.g. a waterproof device or maybe a more breathable device that helps keeping the skin healthy. Especially appreciated is the application of the trigger device embedded in a plaster under the foot to be used as a trigger mechanism to monitor the event of heel strike or heel off. In an embodiment with focus on long life of the trigger device, the trigger device is carried out on a foil as described. The trigger device is mounted on the skin by the use of a plaster adapted to receive the trigger device and further including an adhesive surface for attaching the trigger device on the wanted position. When the plaster is worn out or releases from the position the trigger device can be separated from the disposable plaster and reused just by adding a new plaster.

As can be seen, the invention fully solves the underlying problem by providing a solution that is passive and will not need a direct power supply. Additionally the trigger mechanism can be kept at small dimensions when formed as an adhesive foil that can be mounted directly on the wanted body part of the patient. This is very convenient for patients with gait disorders, since a device working as a heel contact for treating gait disorders can be mounted directly under the foot (heel). No voluminous device is needed so more freedom of movement of the foot is possible and because of the protecting qualities of the foil towards the environment it will be possible for the patient to walk bare footed without any need for the use of supporting socks or bands. The device can be produced with low cost, and thus be affordable to replace on a more often basis when needed. In one embodiment the device can be reused with a new plaster. It can be used daily or as a substitute to the more voluminous state of art solution. Anyhow the device could just as well be mounted in a piece of footwear or at any other means intended for keeping the footswitch in its right place. A special receiving part in the footwear or sock can be designed forming a sleeve or cave that receives the film. The adhesive surface on the film can support the fixation or be used stand alone to mount the film in the shoe. For the practical embodiment of the invention in applications where more trigger devices are used in parallel, more trigger devices could be included in one physical piece of foil to form one combined trigger device. A further advantage for reducing cost, will here be the possibility of having one single resonance circuit with tuning depending on the activated switches. In more advanced systems data patterns including more specific information on the event can be send to the reader. In this way data from a number of sensors or contacts arranged on one piece of foil or plaster can be cared for and forwarded by one transmitter.

In a system for treating incontinence the adhesive foil with the trigger can be placed in a convenient position on the body free of choice. If the patient feel urge, the patient can in an easy and discrete way activate the switch. In one embodiment the trigger device is arranged on a strap that can be fitted to a part of clothing. In yet another embodiment the trigger device is arranged on a wrist band. It is foreseen that the trigger device could be embedded with a wrist watch or a sports or medical device. In addition the trigger device could be arranged in a piece of jewelry as e.g. a bracelet or necklace in order to camouflage the trigger device and still have the trigger device within easy reach.

In yet another embodiment the trigger device is arranged in the frame of a pair of glasses. The RFID coil could in an embodiment be surrounding at least one of the glasses. Thus a very discrete trigger device is presented and the risk of losing the trigger device is lowered.

In another embodiment the trigger device is adapted to be placed in the mouth of the patient. This is advantageous in cases where the patient is an amputee or for other reasons is not capable of using the extremities for activating the trigger device. The trigger device is in one embodiment arranged fixed to one or more teeth such that the trigger device can be activated with the tongue. In another embodiment the trigger device is carried out on a substrate that can be fixed towards the palate in the same way as fixing an artificial denture.

In a special embodiment the trigger device is adapted for being implanted in the human or animal body. Since the trigger device is powered wirelessly, there is no need for exchanging or recharging batteries. It is thus possible to make a smaller device. This makes an advantageous device since the invasive process is less complicated. In addition, the lifetime amount of surgery is minimized since there is no need for explanting and implanting the trigger device because there is no battery that is subject to be exhausted.

It will be appreciated if the invention is not limited to the embodiments explained in this application, but covers all systems for electrical stimulation of nerves, where a trigger device can be used for obtaining a sensed signal and issue a triggering command or as an on demand signal activated by the user, for activating the system for carrying out electrical stimulation of nerves or afferents of nerves. For the sake of easy explanation of the invention, the sensed signals are explained using the gait sensor as an example. It is foreseen that the sensed data could also be biometric parameters as e.g. blood pressure, heart beat, blood composition, temperature, bladder pressure etc.

DESCRIPTION OF THE DRAWINGS

Embodiments of the invention will be described with reference to the accompanying drawing, in which.

Figure 1:
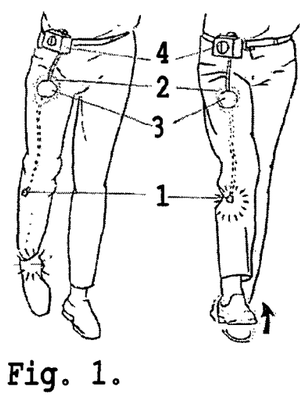
FIG. 1, shows an illustration of a leg region of a patient including a signal generator with antenna and implant with lead and electrode.
Figure 2:
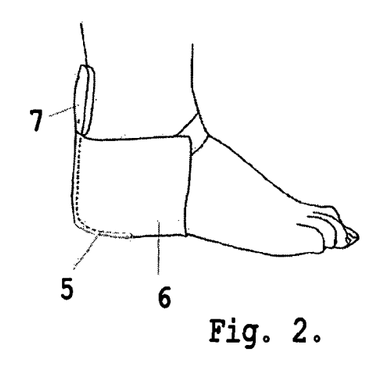
FIG. 2, shows an illustration of a foot with a sock for fixation of a heel switch.

The system for electric stimulation of nerves shown in the drawing includes an implanted electrode 1 electrically connected to an implanted module 2. On the skin of the human body in the proximity of the implanted module 2 is placed an antenna 3, the antenna 3 being connected to the signal generator 4. Thus the signal generator 4 supplies signals for inductively powering the implanted module 2 and providing pulses of electrical current to the implanted electrode 1. The electrode 1 is a CUFF electrode, a tubelike isolating fixture with a number of electrodes the fixture fully embracing the nerve to be stimulated at least over a distance of the length of the nerve. The specific nerve to be stimulated in the present application is the Peroneal nerve. Stimulating the nerve has the effect to cause the foot dorsiflexor muscles to contract. Thus the foot will be lifted and a more natural swing phase of the gait can be achieved. The stimulation signal must be synchronized with the gait of the patient, thus the need for a trigger that reflects a well defined event of the foot. The heel-strike and heel-off events are useful events for determining the gait cycle of the patient and can easily be obtained using a foot switch. To avoid wiring between the controller and the foot switch a wireless communication link is used. An example of a state of art foot switch 5 is shown in FIG. 2. The foot switch device is fixed to the foot with the use of a sock 6. Normally the trigger is equipped with a transmitter 7 and the signal generator 4 is equipped with a receiver. This makes a voluminous trigger device as in the case shown in FIG. 2.

Figure 3:
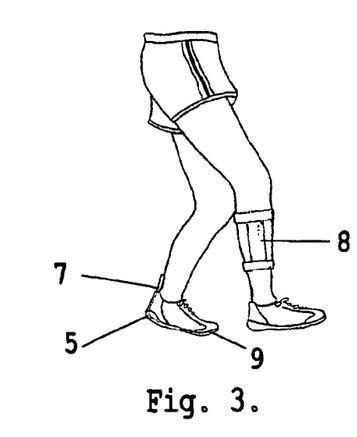
FIG. 3, shows an illustration of a leg region of a patient with a system for surface treatment of nerves.

The use of a wireless trigger device in the form of a foot switch is not exclusively intended for implanted systems for stimulation of nerves. Systems using surface stimulation of nerves in order to achieve the same result as the above mentioned implantable system may also comprise a wireless footswitch. FIG. 3 is showing a surface stimulator device 8 attached to the lower right leg with a wireless footswitch including a transmitter 7 and a foot switch 5 arranged in the shoe 9 on the left foot. It has to be understood that the choice of the left foot is just in order to explain the footswitch and is coincidental. A wireless footswitch could off course be arranged in connection with the left or right foot free of choice or with a wireless footswitch arranged with each foot, requiring that the receiver is able to handle two wireless footswitch devices simultaneously.

Figure 4:
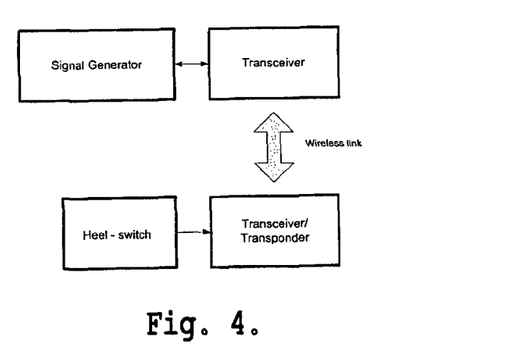
FIG. 4, is a flowchart showing the communication between the signal generator and the trigger device.
Figure 5:
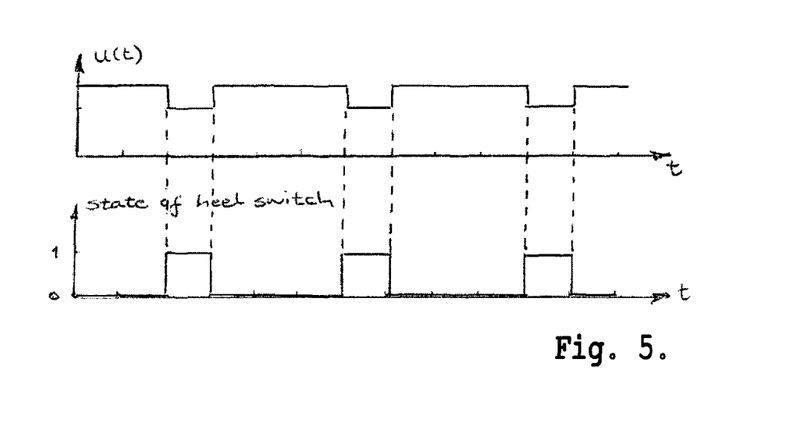
FIG. 5, shows a possible waveform of the signaling between the reader and transponder.

As shown in FIG. 4, showing the principle of the invention, the signal generator 2 is in connection with a transceiver that broadcasts a signal, the signal being transmitted on a continuous basis or send out with regular intervals. The trigger device includes a corresponding transceiver or transponder including an oscillation circuit with a resonance frequency tuned into the signal broadcasted from the transmitter. The oscillation circuit will thus form a load on the signal transmitted from the transmitter. To be able to use the oscillation circuit as a load that corresponds to the event of heel strike or heel off, a switch is arranged in the circuit. When the switch is closed, the closed loop of the oscillation circuit is maintained and the oscillation circuit will appear as a load. If the switch is open, the oscillation circuit is forming an open loop, where it will not appear as a load. Thus when the switch is mounted under the foot, e.g. under the heel of the foot, the oscillation circuit as a load will reflect the state of the foot switch and the transitions will reflect the heel strike and heel off states. The switch can be designed as a normally open or normally closed switch. Thus it is free of choice if the heel strike or heel off shall be monitored with an open or closed foot switch. FIG. 5, shows a simplified waveform of the broadcasted signal from the transmitter and the influence of the closed loop oscillation circuit in the proximity. The second timeline shows the toggling of the switch in the trigger device. The transmitter is equipped with a circuit that is measuring the load and thus it is possible to determine if the switch is open or closed.

Figure 6:
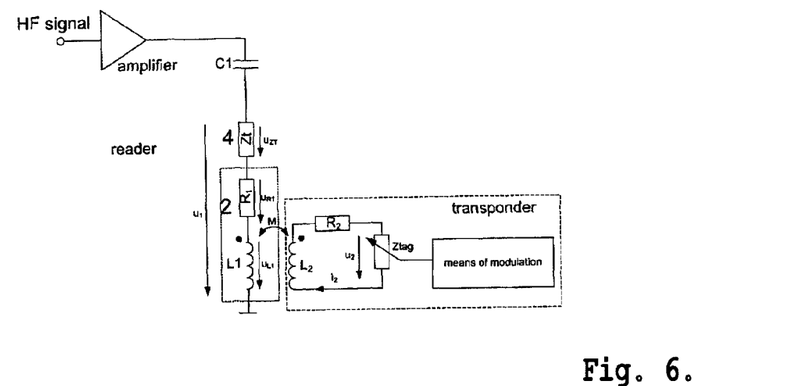
FIG. 6, shows a schematic of the reader and transponder circuit.

FIG. 6, shows a schematic of the transceiver and transponder. A high frequency carrier of constant frequency is generated and amplified and further applied to a series resonance circuit consisting of the primary tuning capacitor C1 and a transmitter coil (reader coil). The reader coil can be split up into the ohmic wire resistance R1 and the ideal inductance L1. The reader coil is inductively coupled to the transponder's receiver coil L2 by a mutual inductance M, which is dependent on the distance between the coils. As further explained in FIG. 6, the transponder side of the resonance circuit, the transponder coil can be split up into the ohmic wire resistance R2 and the ideal inductance L2. Adding the $Z_{tag}$ component to the tag introduces means for modulating the load.

Figure 7:
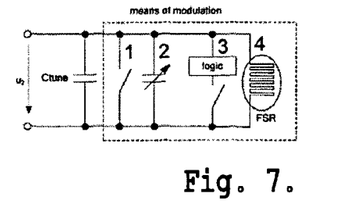
FIG. 7, shows possible means of modulation for the transponder.
Figure 8:
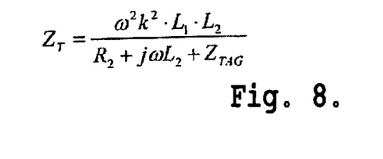
FIG. 8, is a formula for calculating the impedance $Z_T$.
Figure 9:
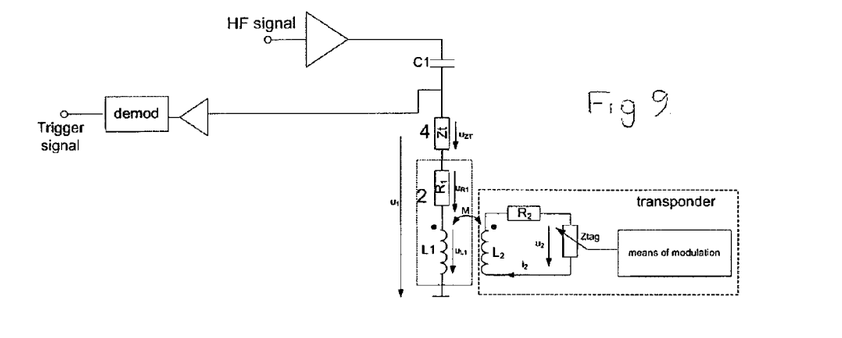
FIG. 9, shows a schematic for a reader capable of demodulating the load signal.
Figures 10, 11:
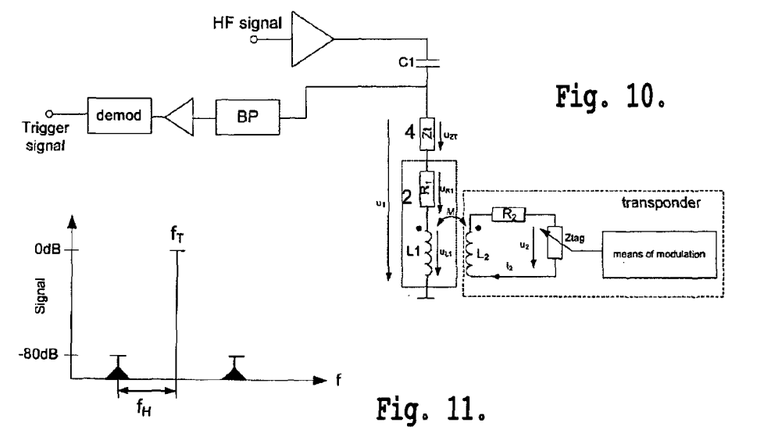
FIG. 10, shows a schematic for a reader as above but with a band-pass filter.
FIG. 11, is a spectral distribution of the from the reader transmitted and received signal.

FIG. 7, shows more possible means for modulating the load, by means of a simple contact, a de-tuning capacitor, by changing the resistance via a force sensitive resistor or in a more sophisticated way by using a logic control circuit for generating a pulse pattern. Modulating the load will result in a complex transformed transponder impedance as indicated in the formula shown in FIG. 8. The change in the impedance transformed to the primary side of the couple is inversely proportional to the change in the secondary side of the couple. This change relates to a measurable change in the voltage U1 that can be measured by directly demodulating the carrier signal as indicated in FIG. 9, showing a part of the schematic with focus on the reader side. The signal is amplified with the use of the amplifier and further led through the demodulator. With this approach the sensitivity of detection and hence obtainable distance between primary and secondary coil limited by the requirement of large difference in amplitude between modulated information and carrier. When modulating with a higher frequency while the foot switch is pressed, e.g. with the use of the control logic shown in FIG. 7, the modulated side band is shifted at a distance corresponding to the subcarrier frequency $f_H$ away from the carrier, as indicated in FIG. 10, allowing an easier band-pass filtering and demodulating with less requirements for dynamic range, hence, a greater distance can potentially be reached. The diagram in FIG. 11 is showing frequency distribution of the signal after the band-pass filtering.

Figure 12:
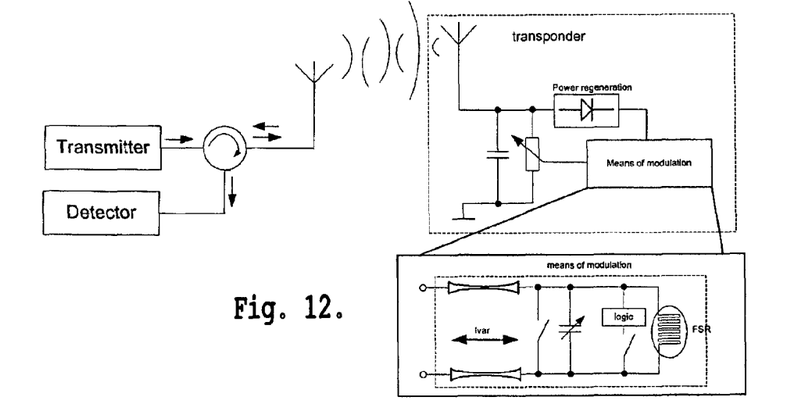
FIG. 12, shows a schematic for a reader and transponder using the backscatter principle.

A special embodiment of the invention shown in FIG. 12 is advantageous if a greater operating range is required. A transmitter generates oscillations within a frequency high enough in order to ensure that the location of the receiver (transponder) is in the far field of the transmitter antenna. Thus, no direct coupling between transmitter and receiver is given, but electromagnetic waves are emitted and received by the receiver antenna. If the transponder contains control logic, then the energy of the received electromagnetic field should be sufficient to power the receiver by means of power regeneration circuitry. The matching between antenna and load impedance determines in any case the wave reflexion coefficients. If perfectly matched, the received wave is perfectly annihilated, and no energy is transmitted back. However, load impedances deviating from the antenna impedance causing part of the received energy to reflect, enabling the receiver by means of a circulator, or by means of a second antenna to receive a signal. The reflexion coefficient can be modulated by resistive load modulation (forces sensitive resistor), capacitive modulation, by means of a mechanic switch, or by changing the transformation of a fixed impedance by changing the length of a micro-strip like conductor, acting like a stub for impedance matching in RF applications. In one possible embodiment the channel is implemented as variable length (for example elastic) conducting polymer or rubber, that changes its length depending on different phases of the gait cycle, and thus changing the transformed impedance of a fixed load.

Figure 13:
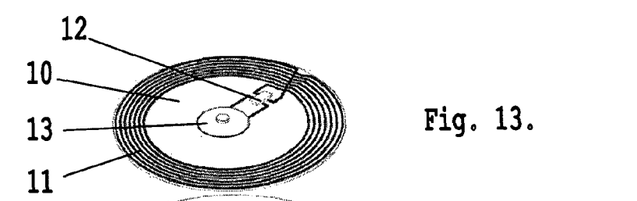
FIG. 13, is a layout for the trigger device, FIG. 14, showing a plaster for the fixation of the trigger device
Figure 14:
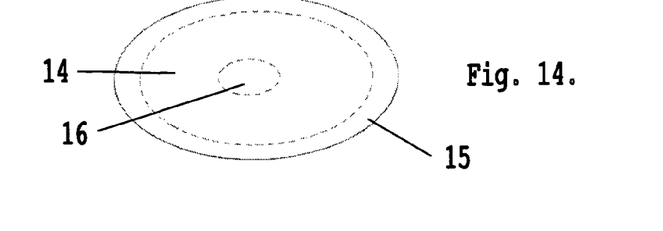
Figure 15:
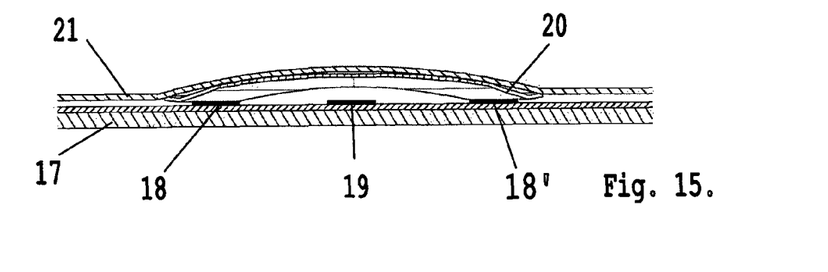
FIG. 15, is a cross section of the trigger device showing a detail of a tactile switch.

FIG. 13, shows a printed circuit board 10 for a preferred embodiment of the trigger device. The oscillation circuit is carried out on a piece of foil. The trigger device comprises a coil 11, an integrated circuit 12 with tuning capacitor and controller for the transponder and a contact 13 connected to the integrated circuit 12 for activation of the transponder. The contact 13 consist of a dome shaped contact that when being manipulated mechanically make an electrical connection between at least two contact points. The track constituting the coil and the connections are carried out as a printed circuit board on a thin film substrate. Additional copper or silver can be added to the track in order to increase the conductivity of the coil. Additionally the track is covered by an isolating layer of foil in such a way that the coil can be routed over the winding of the coil for connection with the integrated circuit. The contact and the integrated circuit must be mounted before an additional layer of foil is added to isolate the device now being fully embedded in isolating material. For protecting the components of the trigger device, achieve mechanical stability and provide electrical isolation, more layers of foil are used to form a sandwich that encloses the trigger device. In order to achieve a higher comfort of use the device can further be embedded in a flexible material like a plaster or a brick of silicone. This embodiment is especially appreciated for the use of the trigger device as an insole in a foot wear. For a practical fixation in a foot wear or directly on the heel or under the foot of the patient, an adhesive layer can be added on one of the outer surfaces. Preferably a protecting foil will avoid the trigger device to adhere before the application on the foot is wanted. This will also make the trigger device suitable for placement in a, for the purpose made, pocket in the shoe or sock. FIG. 14 shows a plaster 14 especially adapted for the application of the trigger device on the wanted position, e.g. under the foot of the patient. The plaster is having a first side which is intended to face the skin of the patient, which fully or partly are supplied with an adhesive layer that makes it possible firstly to fixate the trigger device in a position on the plaster 14 and secondly can be used for fixating the trigger device on the wanted position. This can be achieved since the area of the plaster is larger than the trigger device. In an appreciated embodiment, the plaster is configured in size and shape to receive the trigger device and still have an adhesive rim 15 surrounding the trigger device that is sufficient wide as to secure a reliable fixation of the trigger device at the wanted destination. A center 16 area is also supplied with an adhesive for fixing the trigger device. The area should be kept smaller than the area of the trigger device in order to easily remove a worn out plaster from the trigger device. FIG. 15 is a cross section of a foil showing a detail of the contact. As can be seen the foil comprises a backing element 17 for mechanically stabilizing the platform for the switch. It further comprises a layer of foil on which the printed circuit is arranged. The track includes a first contact point 18 and a second contacting point 19 which can be connected when the dome shaped spring element 20 is manipulated to short circuit the contact points 18, 19. One or more additional layers of foil 21 can be attached to the device for isolating and protecting the trigger device. The mechanical qualities of the layers applied are chosen in order to configure the sensitivity of the switch.

It should be understood that more complex embodiments, as explained in the description, comprising modulating means or logic circuits for generating data streams can be carried out in a similar way on a plaster made of foil. The same will apply for embodiments of trigger devices that comprise more oscillation circuits on a single piece of foil, or comprise a plurality of sensors, e.g. contacts, on a single piece of foil.

The embodiments of the invention are explained used in a system for treating gait disorders with electrical stimulation of nerves. It will be appreciated if the invention in general covers trigger devices of the described type in all systems for electrical stimulation of nerves or afferents of nerves. This could be a system for treating incontinence by electrical stimulation of dorsal nerves. For treating epilepsy, the use of the trigger device could be foreseen in a system for electrical stimulation of the Vagus nerve. Trigger devices adapted to be used as a trigger on demand trigger, activated by the patient, and trigger devices which are capable of obtaining a sensed signal and issue a triggering command, for activating the system for carrying out electrical stimulation of nerves or afferents of nerves is covered by the invention. Both trigger devices adapted to be placed outside the human body and trigger devices adapted to be implanted in the human body are covered by the invention.

The invention claimed is:

1. A system for stimulation of nerves in a user's leg, comprising:
at least one electrode adapted to be coupled to a nerve in a lower leg of the user;
a pulse generator electrically connected to the at least one electrode, the pulse generator being configured to generate a pulse pattern to be transmitted to the at least one electrode and to broadcast signals having a resonant frequency and to be mounted to a hip of the user;
a trigger device adapted to be mounted to an exterior of a foot of the user's leg, the trigger device including an oscillation circuit tuned to the resonant frequency of the signals broadcast by the pulse generator and at least one tactile switch arranged in the oscillation circuit, the trigger device being powered wirelessly by the signals received from the pulse generator;
wherein when the tactile switch is closed between heel-strike and heel-off events, the oscillation circuit is closed and appears as a load to the pulse generator, and when the tactile switch is open between heel-off and heel-strike events, the oscillation circuit is open and does not appear as a load to the pulse generator;
wherein the pulse generator determines a heel strike event based on the load from the oscillation circuit, and then transmits the pulse pattern to the electrode to stimulate the at least one nerve.

2. A system according to claim 1, wherein the pulse generator is configured to continuously generate signals.

3. A system for stimulation of nerves in a user's leg, comprising:
at least one electrode adapted to be coupled to at least one nerve in the user's leg;
a pulse generator electrically connected to the at least one electrode and configured to generate a pulse pattern to be transmitted to the at least one electrode and includes a transmitter to broadcast signals having a resonant frequency, the pulse generator being configured to be positioned on an exterior of the user in an area of the user's hip and to continuously generate signals;
a trigger device adapted to be mounted to an exterior of a foot of the user's leg, the trigger device including an oscillation circuit tuned to the resonant frequency of the signals broadcast by the pulse generator and at least one tactile switch arranged in the oscillation circuit;
wherein when the tactile switch is closed between heel-strike and heel-off events, the oscillation circuit is closed and appears as a load to the pulse generator, and when the tactile switch is open between heel-off and heel-strike events, the oscillation circuit is open and does not appear as a load to the pulse generator;
wherein the pulse generator determines a heel strike event based on the load from the oscillation circuit, and transmits the pulse pattern to the electrode to stimulate the at least one nerve in response to the load;
wherein the trigger device is powered wirelessly by the signals received from the pulse generator;
wherein the at least one electrode and the pulse generator are configured to be positioned on the user at a location proximal of and remote from the trigger device.

4. A system according to claim 3 wherein the trigger device is configured to create modulation products in a side band of the broadcasted signal.

5. A system according to claim , wherein the trigger device includes a logical unit that generates a pre-scaled subcarrier, the subcarrier being modulated onto the broadcasted signal.

6. A system according to claim 3, wherein the trigger device modulates the signal received from the transmitter by producing event-related changes in a reflexion coefficient.

7. A system according to claim 6, wherein the oscillation circuit arranged in the trigger device is configured to produce event-related changes in the reflexion coefficient, the change in the reflexion coefficient reflecting the value of a sensor.

8. A system according to claim 7, wherein the sensor, for obtaining a value, is one of a switch, a variable capacitor, a variable resistor, a force sensitive resistor, a piezo electric element or a logical control circuit generating an analog or digital output.

9. A system according to claim 3, wherein the trigger device includes a logical unit that collects and converts the sensed events or measurements into a data stream.

10. A system according to claim 3, wherein the trigger device is arranged on or in a compound made of one or more layers of flexible material.

11. A system according to claim 10, wherein the compound is supplied with an adhesive on at least one surface or part of a surface.

12. A system according to claim 10, wherein the flexible material comprises plastic foil.

13. A system according to claim 3, wherein the trigger device is adapted to be embedded in or arranged with one of the following:
   A plaster,
   A strap,
   A sports or medical device,
   A piece of jewelry,
   A bracelet or necklace,
   A block of flexible material,
   A block of electrical isolating material, or
   A block of water proof material.

14. A system according to claim 3, wherein the trigger device is adapted to be implanted in the human or animal body.

* * * * *